United States Patent [19]

Martin

[11] 4,330,278
[45] May 18, 1982

[54] ENDODONTIC FLOW-THROUGH ULTRASONIC INSTRUMENT HOLDER DEVICE

[76] Inventor: Howard Martin, 909 Pershing Dr., Silver Spring, Md. 20910

[21] Appl. No.: 164,366

[22] Filed: Jun. 30, 1980

[51] Int. Cl.³ .............................................. A61C 5/02
[52] U.S. Cl. ....................................... 433/81; 433/86; 433/129; 279/20; 408/56; 128/247; 128/24 A
[58] Field of Search ................ 433/81, 86, 82, 80, 433/88, 89, 90, 147, 129; 279/20; 408/56; 128/247, 24 A

[56] References Cited

U.S. PATENT DOCUMENTS

| | | | |
|---|---|---|---|
| 1,316,685 | 9/1919 | Cates | 433/147 |
| 1,417,379 | 5/1922 | Harvin | 433/91 |
| 2,531,730 | 11/1950 | Henderson | 433/91 |
| 2,680,333 | 6/1954 | Calosi | 51/59.55 |
| 3,124,878 | 3/1964 | Bodine, Jr. et al. | 433/119 |
| 3,724,076 | 4/1973 | Schmitz | 433/90 |
| 3,806,270 | 4/1974 | Tanner et al. | 408/56 |
| 3,871,097 | 3/1975 | Melde | 433/82 |
| 3,956,826 | 5/1976 | Perdreaux, Jr. | 128/24 A |
| 4,223,676 | 9/1980 | Wuchinich et al. | 128/24 A |

FOREIGN PATENT DOCUMENTS 836227 4/1952 Fed. Rep. of Germany ........ 433/80
944517 5/1956 Fed. Rep. of Germany ........ 433/80

*Primary Examiner*—Gene Mancene
*Assistant Examiner*—John J. Wilson
*Attorney, Agent, or Firm*—Walter G. Finch

[57] ABSTRACT

The invention is an improved endodontic apparatus device for holding instruments, particularly endodontic drill files that are energized and vibrated by ultrasonic means. The invention also provides for the flow-through of solutions during debriding and irrigating of root canals. The invention consists of a hollow tube-like means for conducting solution and directing it in the axial direction of the endodontic drill file; the hollow tube-like means incorporates a special holding means at the outboard end thereof for mounting the drill file in a position so that ultrasonic waves can be transmitted to the drill file to cause it to vibrate in a manner that improves debriding of the root canals. The special holding means at the end of the hollow tube-like means retains the drill file in a firm position to receive the transmitted ultrasonic waves.

10 Claims, 7 Drawing Figures

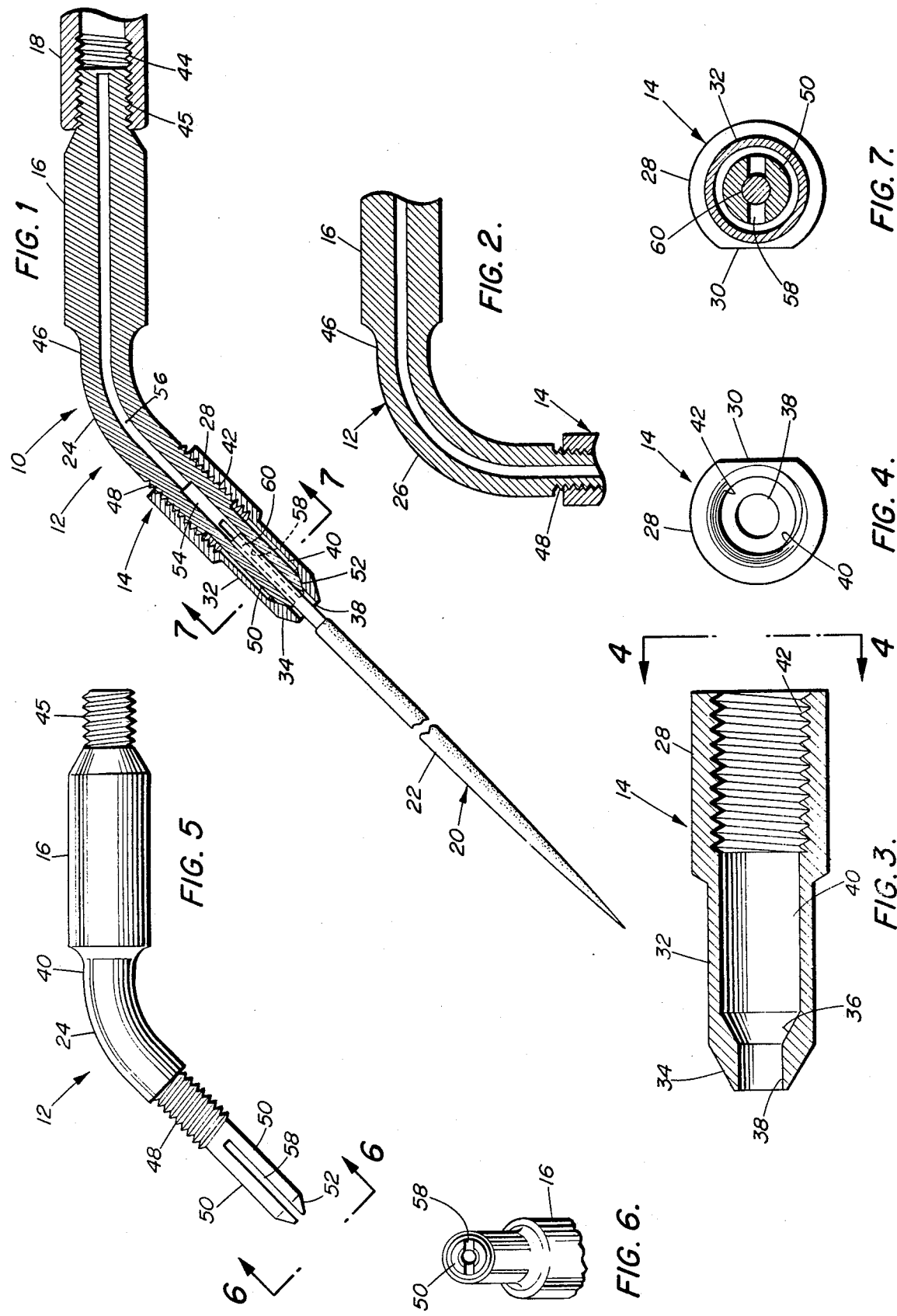

ENDODONTIC FLOW-THROUGH ULTRASONIC INSTRUMENT HOLDER DEVICE

BACKGROUND AND SUMMARY OF THE INVENTION

The invention relates to dental instruments and systems and in particular to endodontic instruments and systems. Specifically, the invention relates to an ultrasonic system and an endodontic drill file for debriding root canals.

The invention provides a special flow-through means for directing a solution around and past the drill file and along the longitudinal axis of the instrument to irrigate the root canal which is being debrided by the endodontic drill file.

The endodontic flow-through ultrasonic instrument holder device of this invention may also be referred to as an endodontic endosonic drill-file holder.

In the prior art the endodontic drill files were primarily operated manually, simultaneously in a more or less vertical-like movement in the more or less longitudinal direction of the root canal and with a partial back and forth rotating motion. Mechanical methods were inadequate.

Original ultrasonic trials in the prior art were accomplished by rigid connection to the ultrasonic transducer mechanism and were not successful.

Subsequent to the original ultrasonic trials an improved ultrasonic attachment was developed, which is the subject of a copending United States Patent application in which the present inventor is a coinventor. The copending application is Ser. No. 108,969, filed Dec. 31, 1979, now U.S. Pat. No. 4,295,827, Oct. 20, 1981, for an Endodontic Flow-Through Ultransonic Instrument Holder Attachment.

The present invention is an improvement over the attachment in the copending application. The prior invention uses a rubber-like holding means within the attachment which requires some manual restraint at the upper end during use, because the holding means does not retain the drill file in a firm position. The attachment in the copending application is an improvement over the prior art, the present invention is an improvement over the invention of the copending application.

Also, in the prior art, irrigation of root canals during treatment was by a separate means which required the drilling action for debriding to cease while the irrigation was performed. Other irrigation means directed the solution from an external point. This caused considerable "splash-back" and was not satisfactory.

In the present invention the aforementioned problems of the prior art are overcome. The endodontic drill-file is mounted firmly at one end of the file by a point contact means, instead of a rigid connection at the central axis of the ultrasonic transducer, and in a manner that manual restraint on the upper end of the file is not required during ues.

The mode of mounting the drill file in the present invention permits the endodontic drill file to vibrate in a series of criss-crossing motions and at the same time the free end tends to vibrate in a movement that is circularlike and/or ellipsoidal or oval.

Coupled with the unique and novel means of mounting the endodontic drill file in the holder, is a hollow tubelike means that transports solution for irrigating the root canal and directing it along the longitudinal axis of the drill file and directly into the root canal. In the present invention the solution is directed around the end of the drill-file where it is secured in place and down the sides of the drill file in the slot-like configuration of the securing means.

The irrigation, which may be used to disinfect, cavitate, shear and acoustic streaming, and to flush out debris from the root canal debriding operations of the drill file, can be controlled and used at will without withdrawing the drill file from the root canal.

The endodontic flow-through ultrasonic instrument holder device may be made to project the instrument at 90° from the energy supply line or at a plurality of projection positions therefrom, such as at 45°.

It is, therefore, an object of the invention to provide a holder device for endodontic instruments.

It is another object of the invention to provide a holder device specifically for endodontic drill files.

It is also an object of the invention to provide a holder device for endodontic instruments which is energized and operated by ultrasonic means.

It is still another object of the invention to provide a holder device for endodontic instruments that has flow-through means for directing a solution axially along the instrument.

It is yet another object of the invention to provide a holder device for endodontic instruments that mounts the endodontic instruments by point contact to produce a novel vibrating pattern.

It is yet still another object of the invention to provide a holder device for endodontic instruments that holds the instruments firmly without the need for any manual restraint.

It is also still another object of the invention to provide a holder device for endodontic instruments with special means for directing a solution in the flow-through means around the drill file in the point contact position.

Further objects and advantages of the invention will become more apparent in the light of the following description of the preferred embodiments.

BRIEF DESCRIPTION OF THE DRAWINGS

FIG. 1 is a longitudinal cross section of an endodontic instrument holder device attached to the end of an ultrasonic mechanism, showing an endodontic instrument mounted therein at 45° to the energy supply line;

FIG. 2 is a partial longitudinal cross section similar to FIG. 1 with energy supply line at 90° to the instrument mounting line;

FIG. 3 is a longitudinal cross section through an instrument locking means of an endodontic instrument holder device;

FIG. 4 is an end view of FIG. 3;

FIG. 5 is side view an endodontic instrument holder device tip;

FIG. 6 is an end view of FIG. 5;

FIG. 7 is a cross sectional view on line 7—7 of FIG. 1.

DESCRIPTION OF THE PREFERRED EMBODIMENTS

Referring to the drawings, and particularly to FIG. 1, an endodontic flow-through ultrasonic instrument holder device is shown at 10.

The instrument holder device 10 is comprised primarily of a tip member 12 and a locking means 14.

The tip member 12 is generally cylindrical-like and consists of an ultrasonic connecting end 16, a reduced portion 46, nibs 50, and nib threads 48 as shown in FIGS. 5 and 6.

The reduced portion 46 is shown in FIG. 1 with a bend 24 at approximately 45° and with a bend 26 at approximately 90° in FIG. 2. It is to be understood that it is within the scope and intent of this invention to configure the tip member 12 at any angle from a straight in-line configuration (not shown) to the 90° as shown in FIG. 2. For general convenience in dental work the 45° angle shown in FIG. 1 is the preferred embodiment.

It is also to be understood that it is within the scope and intent of the invention for the tip member 12 to be made without the reduction of the portion 46 from the size of the connecting end 16, and that the cross-sectional configuration may be round, square, or any other geometrical configuration.

The connecting end 16 is shown with an external thread 45 for connecting to an ultrasonic transducer mechanism 18 with inside threads 44. It is to be understood that it is within the scope and intent of the invention for the connecting end 16 to have inside threads for connecting to outside threads of an ultrasonic transducer mechanism 18.

Referring to FIGS. 5 and 6, the nibs 50 have a tapered end 52, the purpose of which is described hereinafter. A counter-bore 54 in the end of the nibs 50 communicates with a passageway 56 running through the connecting end 16, the reduced portion 46 and the screw threads 48. The interface for communication of the counter-bore 54 and the passageway 56 is shown within the portion of the nib threads 48. However, it is to be understood that it is within the scope and intent of the invention for this interface for communication of the counter-bore 54 and the passageway 56 to occur anywhere along the axis of the tip member 12.

The nibs 50 are formed by a slot 58 that is cut into the end of the tip member 12. Two nibs 50 are shown in FIGS. 5 and 6, but it is to be understood that a plurality of nibs 50 is within the scope and intent of the invention, such as three nibs 50, four nibs 50, or any other number convenient for the purpose of holding the ultrasonic instrument as described hereinafter.

Turning now to FIGS. 3 and 4, the locking means 14 is hollow and cylindrical-like consists of a first body section 28 and a second body section 32. The second body section 32 is shown reduced in relation to the first body section 28. However, it is to be understood that it is within the scope and intent of the invention for the first and second body sections to be of the same cross sectional size; also, that the cross-sectional configuration may be round, square, hexagonal, or any other geometrical configuration.

A portion of the first body section 28 has been removed to form a flat face 30 to facilitate the application of a wrench for tightening during assembly. The same facility can be accomplished by using a material with a cross section having flat sides, such as the aforementioned square or hexagonal configuration.

The locking means 14 has a passageway 40 therethrough which tapers 36 at the inside end thereof and then communicates with the aperture 38 in the end of the locking means 14. An inside thread 42 in the first body section 28 mates with the outside nib threads 48 for assembly as hereinafter described.

The distal end of the second body section 32 is tapered 34 more or less parallel to the inside taper 36.

When the endodontic flow-through ultrasonic instrument holder device 10 is assembled and used, the nibs 50 of tip member 12 are inserted into the passageway 40 of the locking means 14 until the outside threads 48 of the tip member 12 enage the inside threads 42 in the locking means 14. After starting the engagement of the threads 42 and 48, the assembly is connected to the ultrasonic transducer mechanism 18 by engaging the threads 45 with the threads 44 in the ultrasonic transducer mechanism 18 and tightened.

An ultrasonic instrument 20, such as an endodontic drill file 22, is inserted through the aperture 38 and into the counter-bore 54, thus effectively placing it between the nibs 50. The assembled end 60 of the drill file 22 is sized and configured to fit into the counter-bore 54.

The locking means 14 is then tightened on the tip member 12 by the further engagement of the screw threads 42 and 48. As the tightening proceeds the tapered end 52 of the tip member 12 approaches and passes into the aperture 38. As further tightening of locking means 14 occurs, the tapered end 52 interfaces the corner intersection of aperture 38 and inside taper 36, thus squeezing the nibs 50 together (narrowing the slots 58) and thus gripping the end 60 of the drill file 22 and holding it firm for the ultrasonic pulses when the device is operated. The relationship of the interface of the end 60 of the drill file 22, the nibs 50, and the slots 58 can be seen in FIG. 7.

The end 60 of the drill file 22 is configured and inserted in the counter-bore 54 between the nibs 50 to extend to a point in the counter-bore 54 so that it does not extend to the throat end of the slots 58, that is, the throat end of the slots 58 nearest the nib threads 48.

The end 60 of the drill file 22, as described hereinbefore, is spaced from the throat end of the slots 58, thus permitting the passageway 56, which communicates with the counter-bore 54, to have communication with the slots 58.

Solution passing through the flow-through passageway 56, then passes through the portion of the counter-bore 54 beyond the end 60 of the drill file 22, then is directed into the slot 58 on each side of the end 60 of the drill file 22, thereby passing axially along the sides of the drill file 22 within the passageway 40 of the locking means 14, then out through the aperature 38 via the communication afforded by the slots 58 at the tapered end 52 which has been extended into the aperture 38 by the tightening of the locking means 14. The solution thus irrigates the root canal as it is directed axially along the drill file 22.

It is to be understood that the ultrasonic connecting end 16 may be made to fit any ultrasonic transducer mechanism 18 merely by the use of a suitable adapter fitting or by sizing and configuring the end (at the threaded end 45) to fit the transducer mechanism 18 concerned.

It is to be understood that while the description for this invention has been related to an endodontic drill file 22, the instrument holder device 10 may be used for, or suitably adapted to, other endodontic or other dental instruments.

When ultrasonic vibrations are produced by the transducer mechanism 18, the vibrations are transmitted through the structure, hereinbefore described, to the instrument 20, in this case drill file 22, and cause it to vibrate.

The vibrations of the unrestrained end of the instrument 20 occur in all directions due to being a very thin, freely, extending, clamped-free type of cantilever member, subsequently the vibrating action takes on a more or less circular-like movement or vibration. This energized circular-like vibrating movement debrides the root canal walls as the drill file 22 is moved in and out of the root canal passageway.

As needed, and at the proper moment, the dentist can irrigate and disinfect the root canal by releasing, through controls, a solution from a source through the passageway 56 and thereafter into the root canal as hereinbefore described.

This same procedure can also be used when other endodontic or dental instruments are used. The irrigation cleans out and cavitates the debris from the debriding action which in endodontic procedure removes tooth structure from the wall of the root canal.

The direct flow of the solution along the axial direction of the drill file 22 prevents splashback of the solution.

Thus, the improved instrument holder device 10 facilitates both instrumentation and irrigation of root canals or other endodontic or other dental work to which it may be adaptable. Most importantly, this is accomplished by a structure that holds the drill file 22 firmly and without the need for manual restraint.

The instrument holder device 10 becomes a velocity transformer for the ultrasonic waves. It is also to be noted that when a solution is being passed through the passageway 56, as hereinbefore described, the ultrasonic waves may also be transmitted through the solution as well as the instrument holder device 10 structure.

The instrument holder device 10 may be made of any suitable material, particularly metal, such as stainless steel or the equivalent that will be compatible and in resonance with an ultrasonic unit for proper impedance.

It is also to be noted that in endodontic apparatus the instrument holder device 10 may be configured with many dimensions of several millimeters, however, it is to be understood that for other instruments using this structure a configuration of other dimensions is within the scope and intent of this invention.

The effectiveness of the imposed ultrasonic forces in improving the cutting effectiveness is a function of the ratio of the maximum vibrating tip velocity of the drill file 22 to the peripheral velocity of the drill file 22 relative to the work surface of the root canal.

As can be readily understood from the foregoing description of the invention, the present structure can be configured in different modes to provide the ability to hold an instrument for ultrasonic vibration with a means for flowthrough of a solution, for endodontic or other dental work.

Accordingly, modifications and variations to which the invention is susceptible may be practiced without departing from the scope and intent of the appended claims.

What is claimed is:

1. An instrument holder device, comprising:
an instrument, said instrument being for dental work;
a holding means, said holding means having a first portion and a second portion, said first portion consisting of at least two nibs and cylindrical-like part, said nibs being located at the distal end of said first portion, said cylindrical-like part being located immediately adjacent to and integral with said nibs, said cylindrical-like part having external screw threads thereon, said nibs being spaced apart around the periphery of said distal end of said first portion, said nibs having a clearance space between the sides thereof and the sides of adjacent nibs, said nibs being tapered on the exterior of the distal end thereof, said holding means having a continuous passageway therethrough, said first portion and said second portion being adjacent to, a continuation of, and integral with, each other, said passageway being continuous through both said first and second portions, said passageway having a counter-bore, said counter-bore extending inwardly from the distal end of said nibs, one end of said instrument being removably inserted into said counter-bore, said instrument having a mounting end thereon configured to fit withing said counter-bore, said second portion having external screw threads thereon, said external threads on said second portion being located on the distal end thereof opposite to said distal end of said first portion; and
a locking means, said locking means being configured as a hollow, cylindrical-like body, said body having a first end and a second end, said body having a passageway therethrough, said passageway having internal screw threads in said passageway at said first end of said body, said internal screw threads mating with said external screw threads on said cylindrical-like part of said first portion of said holding means, said body of said locking means being reduced in configuration in relation to said passageway therethrough at said second end thereof, said first end of said holding means being removably inserted into said first end of said locking means and removably assembled thereto by engaging said external screw threads on said first portion of said holding means with said internal threads in said locking means, thereby locking said end of said instrument within said nibs of said holding means, said locking means being removably affixed to said holding means to secure said instrument in said holding means, said instrument being locked in place by tightening said locking means on said holding means, whereupon said tapered ends of said nibs interface with the internal periphery of said passgeway and tighten upon said mounting end of said instrument as said locking means is further tightened, a portion of the exterior of said locking means being configured to provide a suitable surface for attachment of a wrench means for tightening said locking means when assembled with an instrument therein, said passageway in said holding means cooperates with the internal configuration of said locking means so as to formulate a communicating series of passageways within said instrument holder device for the passage of a solution therethrough, said series of passageways consisting of said passageway through said holding means, including said counter-bore, the opening between spaced apart nibs, and the passageway in said locking means, said solution being discharged axially along said instrument.

2. The instrument holder device as recited in claim 1, wherein said holding means is configured so that said first portion thereof is bent at a 45° angle to the horizontal axis of said second portion thereof.

3. The instrument holder device as recited in claim 1, wherein said holding means is configured so that said first portion thereof is bent at a 90° angle to the horizontal axis of said second portion thereof.

4. The instrument holder device as recited in claim 1, wherein said second portion of said holding means is removably affixed to an ultrasonic transducer mechanism by attachment of said ultrasonic transducer mechanism to said external screw threads at said distal end of said second portion of said holding means.

5. An instrument holder device, comprising:
an instrument, said instrument being for dental work;
a holding means, said holding means having a first portion and a second portion, said first portion consisting of at least two nibs and a cylindrical-like part, said nibs being located at the distal end of said first portion, said cylindrical-like part being located immediately adjacent to and integral with said nibs, said cylindrical-like part having external screw threads thereon, said nibs being spaced apart around the periphery of said distal end of said first portion, said nibs having a clearance space between the sides thereof and the sides of adjacent nibs, said holding means having a continuous passageway therethrough, said first portion and said second portion being adjacent to, a continuation of, and integral with each other, said passageway being continuous through both said first and second portions, said passageway having a counter-bore, said counter-bore extending inwardly from the distal end of said nibs, one end of said instrument being removably inserted into said counter-bore, said second portion having external screw threads thereon, said external screw threads on said second portion being located on the distal end thereof opposite to said distal end of said first portion, said second portion of said holding means being removably affixed to an ultrasonic transducer mechanism by attachment of said ultrasonic transducer mechanism to said external screw threads at said distal end of said second portion of said holding means; and
a locking means, said locking means being configured as a hollow, cylindrical-like body, said body having a first end and a second end, said body having a passageway therethrough, said passageway having internal screw threads in said passageway at said first end of said body, said internal screw threads mating with said external screw threads on said cylindrical-like part of said first portion of said holding means, said body of said locking means being reduced in configuration in relation to said passageway therethrough at said second end thereof, said first end of said holding means being removably inserted into said first end of said locking means and removably assembled thereto by engaging said external screw threads on said first part of said holding means with said internal threads in said locking means, thereby locking said end of said instrument within said nibs of said holding means, said locking means being removably affixed to said holding means to secure said instrument in said holding means.

6. The instrument holder device as recited in claim 5, wherein said holding means is configured so that said first portion thereof is bent at a 45° angle to the horizontal axis of said second portion thereof.

7. The instrument holder device as recited in claim 5, wherein said holding means is configured so that said first portion thereof is bent at a 90° angle to the horizontal axis of said second portion thereof.

8. The instrument holder device as recited in claim 5, wherein said nibs are tapered on the exteriors of the distal end thereof.

9. The instrument holder device as recited in claim 8, said instrument has a mounting end thereof configured to fit within said counter-bore, said instrument being locked in place by tightening said locking means on said holding means, whereupon said tapered ends of said nibs interface with the internal periphery of said passageway and tighter upon said mounting end of said instrument as said locking means is further tightened.

10. The instrument holder device as recited in claim 5, wherein said instrument is an endodontic drill file.

* * * * *